United States Patent [19]

Yankee

[11] 4,085,271
[45] Apr. 18, 1978

[54] 5-OXA-CIS-13-PGF$_1$ COMPOUNDS

[75] Inventor: Ernest W. Yankee, Portage, Mich.

[73] Assignee: The Upjohn Company, Kalamazoo, Mich.

[21] Appl. No.: 774,082

[22] Filed: Mar. 3, 1977

Related U.S. Application Data

[62] Division of Ser. No. 595,869, Jul. 14, 1975, Pat. No. 4,026,909.

[51] Int. Cl.$^2$ .......................................... C07C 177/00
[52] U.S. Cl. ................................ 560/121; 260/514 D
[58] Field of Search ....................... 260/468 D, 514 D

[56] References Cited

U.S. PATENT DOCUMENTS 4,046,801  9/1977  Kluge et al. ......................... 560/121

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes at the prostaglandins. Among these purposes are blood pressure lowering, labor induction at term, reproductive-cycle regulation, gastric antisecretory action, and the like.

25 Claims, No Drawings

5-OXA-CIS-13-PGF₁ COMPOUNDS

The present application is a divisional application of Ser. No. 595,869, filed July 14, 1975, now issued as U.S. Pat. No. 4,026,909 on May 31, 1977.

The present invention relates to prostaglandin analogs for which the essential material constituting a disclosure therefor is incorporated by reference here from U.S. Pat. No. 4,026,909, issued May 31, 1977.

I claim:

1. A compound of the formula

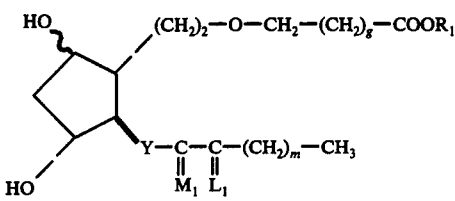

wherein $g$ is 2, 3, or 4;
wherein Y is cis-CH=CH-;
wherein $M_1$ is

or

wherein $R_5$ and $R_6$ are hydrogen or methyl, with the proviso that one of $R_5$ and $R_6$ is methyl only when the other is hydrogen;
wherein $L_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $m$ is one to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of 1 to 3 carbon atoms, inclusive, or a pharmacologically acceptable cation.

2. A compound according to claim 1, wherein $g$ is 4.
3. A compound according to claim 2, wherein $m$ is 3.
4. A compound according to claim 3, wherein at least one of $R_3$ and $R_4$ is fluoro.
5. A compound according to claim 4, wherein $R_3$ and $R_4$ are both fluoro.
6. A compound according to claim 5, wherein $R_5$ and $R_6$ are hydrogen.
7. 15-epi-2a,2b-Dihomo-16,16-difluoro-5-oxa-cis-13-PGF₁α, methyl ester, a compound according to claim 6.
8. A compound according to claim 3, wherein at least one of $R_3$ and $R_4$ is methyl.
9. A compound according to claim 8, wherein $R_3$ and $R_4$ are both methyl.
10. A compound according to claim 9, wherein $R_5$ and $R_6$ are both hydrogen.
11. 15-epi-2a,2b-Dihomo-16,16-dimethyl-5-oxa-cis-13-PGF₁α, methyl ester, a compound according to claim 10.
12. A compound according to claim 3, wherein $R_3$, $R_4$, and $R_5$ are hydrogen.
13. 15-epi-2a,2b-Dihomo-5-oxa-cis-13-PGF₁α, methyl ester, a compound according to claim 12.
14. A compound according to claim 1, wherein $g$ is 2.
15. A compound according to claim 14, wherein $m$ is 3.
16. A compound according to claim 15, wherein at least one of $R_3$ and $R_4$ is fluoro.
17. A compound according to claim 16, wherein both $R_3$ and $R_4$ are fluoro.
18. A compound according to claim 17, wherein $R_5$ and $R_6$ are hydrogen.
19. 15-epi-16,16-Difluoro-5-oxa-cis-13-PGF₁α, methyl ester, a compound according to claim 18.
20. A compound according to claim 15, wherein at least one of $R_3$ and $R_4$ is methyl.
21. A compound according to claim 20, wherein $R_3$ and $R_4$ are both methyl.
22. A compound according to claim 21, wherein $R_5$ and $R_6$ are hydrogen.
23. 15-epi-16,16-Dimethyl-5-oxa-cis-13-PGF₁α, methyl ester, a compound according to claim 22.
24. A compound according to claim 15, wherein $R_3$, $R_4$, and $R_5$ are hydrogen.
25. 15-epi-5-oxa-cis-13-PGF₁α, methyl ester, a compound according to claim 24.

* * * * *

UNITED STATES PATENT OFFICE
CERTIFICATE OF CORRECTION

Patent No. 4,085,271  Dated  April 18, 1978

Inventor(s)  Ernest W. Yankee

It is certified that error appears in the above-identified patent and that said Letters Patent are hereby corrected as shown below:

Column 1, at lines 37-38 and at 44-45

" 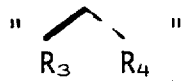 "    should read --    --.

Signed and Sealed this

*Thirty-first* Day of *October 1978*

[SEAL]

Attest:

RUTH C. MASON
*Attesting Officer*

DONALD W. BANNER
*Commissioner of Patents and Trademarks*